United States Patent
Klupt (10) Patent No.: US 7,080,980 B2
(45) Date of Patent: Jul. 25, 2006

(54) DENTAL HYGIENE DEVICE

(76) Inventor: Michael Klupt, 7 Thistledell Ct., Owings Mills, MD (US) 21117

(*) Notice: Subject to any disclaimer, the term of this patent is extended or adjusted under 35 U.S.C. 154(b) by 139 days.

(21) Appl. No.: 10/883,653

(22) Filed: Jul. 6, 2004

(65) Prior Publication Data

US 2005/0004498 A1 Jan. 6, 2005

Related U.S. Application Data

(60) Provisional application No. 60/484,291, filed on Jul. 3, 2003.

(51) Int. Cl.
*A61C 17/02* (2006.01)
*A46B 13/04* (2006.01)

(52) U.S. Cl. .............. 433/80; 433/89; 15/29; 15/167.1; 601/162; 401/282

(58) Field of Classification Search ................ 433/80, 433/89; 15/29, 167.1; 401/282, 289; 601/162, 601/165
See application file for complete search history.

(56) References Cited

U.S. PATENT DOCUMENTS

| | | | | |
|---|---|---|---|---|
| 3,809,977 A * | 5/1974 | Balamuth et al. | ........... | 318/116 |
| 3,977,084 A * | 8/1976 | Sloan | ........... | 433/131 |
| 4,141,352 A * | 2/1979 | Ebner et al. | ........... | 601/162 |
| 4,315,741 A * | 2/1982 | Reichl | ........... | 433/82 |
| 4,365,376 A * | 12/1982 | Oda et al. | ........... | 15/22.1 |
| 5,033,961 A * | 7/1991 | Kandler et al. | ........... | 433/89 |
| 5,142,723 A * | 9/1992 | Lustig et al. | ........... | 15/22.1 |
| 5,150,492 A * | 9/1992 | Suroff | ........... | 15/22.1 |
| 5,197,458 A * | 3/1993 | Ito et al. | ........... | 601/162 |
| 5,205,744 A * | 4/1993 | Weissman | ........... | 433/122 |
| 5,286,192 A * | 2/1994 | Dixon | ........... | 433/80 |
| 5,301,381 A * | 4/1994 | Klupt | ........... | 15/22.1 |
| 5,321,865 A * | 6/1994 | Kaeser | ........... | 15/22.1 |
| 5,321,866 A * | 6/1994 | Klupt | ........... | 15/22.1 |
| 5,344,317 A * | 9/1994 | Pacher et al. | ........... | 433/85 |
| 5,476,384 A * | 12/1995 | Giuliani et al. | ........... | 433/216 |
| 5,634,791 A * | 6/1997 | Matsuura et al. | ........... | 433/87 |
| 6,030,215 A * | 2/2000 | Ellion et al. | ........... | 433/89 |
| 6,164,967 A * | 12/2000 | Sale et al. | ........... | 433/80 |
| 6,220,772 B1 * | 4/2001 | Taylor | ........... | 401/176 |
| 6,247,929 B1 * | 6/2001 | Bachman et al. | ........... | 433/80 |
| 6,375,459 B1 * | 4/2002 | Kamen et al. | ........... | 433/80 |
| 6,622,333 B1 * | 9/2003 | Rehkemper et al. | ........... | 15/29 |
| 6,689,078 B1 * | 2/2004 | Rehkemper et al. | ........... | 601/162 |
| 6,739,782 B1 * | 5/2004 | Rehkemper et al. | ........... | 401/279 |
| 6,766,549 B1 * | 7/2004 | Klupt | ........... | 15/22.2 |
| 6,884,069 B1 * | 4/2005 | Goldman | ........... | 433/88 |
| 2004/0209222 A1 * | 10/2004 | Snyder et al. | ........... | 433/80 |

\* cited by examiner

*Primary Examiner*—Ralph A. Lewis
(74) *Attorney, Agent, or Firm*—Rosenberg, Klein & Lee (57) ABSTRACT

A dental hygiene system provided with interchangeable dental heads permits power-enhanced brushing and concurrent fluid irrigation to optimize a user's personal dental hygiene efforts. The system has a handle assembly with an irrigation nozzle in close proximity to displaceable bristles driven by a battery-operated handle motor. Pumping of irrigation fluid such as an antiseptic solution into the oral cavity is also motor driven. A telescoping chamber with irrigation fluid fits on the piston-like base end of the handle and is refilled by docking the handle assembly on a complementary docking station that includes a detachable fluid reservoir, microswitch controls and a base fluid pump. Docking of the handle assembly triggers the microswitches and opens a check valve in the bottom of the handle chamber, which activates the flow of fluid from the reservoir into the chamber. An optional fiberoptic subassembly illuminates the oral cavity.

19 Claims, 9 Drawing Sheets

DENTAL HYGIENE DEVICE

RELATED PATENT APPLICATION

The present patent application is based on U.S. Provisional Patent Application No. 60/484,291, filed on 3 Jul. 2003.

FIELD OF THE INVENTION

The field of this invention is dental hygiene devices. In particular this invention relates to dental hygiene devices in the form of powered toothbrushes. Still further this invention is directed to the field of dental hygiene devices where an antiseptic liquid is introduced into the oral cavity during a tooth brushing procedure.

BACKGROUND OF THE INVENTION

The present invention relates to a dental hygiene device, and more specifically an electrically power operated toothbrush system which may be battery operated which permits brushing of teeth and also irrigation of the periodontal and dental areas with an antiseptic solution or the like. In particular, the invention is directed to a toothbrush system a mechanism which irrigates periodontal structures and teeth with a fluid such as an antiseptic solution which also concurrently illuminates the area in the mouth being worked on thereby allowing a user to have a visual assessment of the effectiveness of the user's personal dental hygiene efforts.

The present invention is further directed to a battery-powered toothbrush system with enhanced brushing effected by motor-driven oscillating and/or rotating bristles having an irrigation mechanism which includes a telescoping fluid chamber sliding along a piston-like lower portion of a toothbrush handle. A complementary base member defining a docking station is provided which includes a detachable fluid reservoir and microswitch-controlled filling mechanism which provides for the integrated and user-friendly multi-functionality of the dental hygiene device disclosed herein.

Additionally, the invention is directed to a dental hygiene system having dental hygiene heads that are interchangeable and connectable to the handle housing. The interchangeable dental hygiene heads provide a variety of bristles, such as soft, hard, abrasive, etc; a number of different fluid outlet nozzles; and a fiberoptic illumination head, thereby allowing a user to combine enhanced brushing, fluid delivery under pressure, and illumination to further a user's optimal personal dental hygiene.

The present invention is particularly directed to a dental hygiene system with interchangeable dental hygiene heads, having bristles and fiberoptic lighting combined with an irrigating sub-assembly that encompasses a telescoping fluid chamber in the toothbrush handle with the lower end of the toothbrush assembly formed as the piston seated in the fluid chamber. The telescoping fluid chamber is adapted to be refilled by the docking of the toothbrush assembly in a complementary docking base member that has an interchangeable fluid reservoir.

The invention is directed as well to the dental hygiene device docking base member that includes a detachable fluid reservoir and microswitch-controlled valve mechanism for the refilling of the telescoping handle chamber at least in large part automatically. The docking base member is adapted to receivingly and matingly dock the aforesaid toothbrush assembly and provide a user with a refilling process that starts and stops with practically no need for user input.

PRIOR ART

There have been numerous attempts in the prior art to develop an electric toothbrush system that delivers a fluid, such as toothpaste gel or an antiseptic solution, to the periodontal areas while the user brushes. None has seen widespread use or commercial success reflecting the more or less inelegant means chosen to design such prior art devices.

The adoption of such a dual function toothbrush system by users requires that such a device be substantially automatic, formed with a comfortable roughly fusiform shape with ergonomically placed control buttons, be fool-proof and safe.

The present invention has overcome the disadvantages of the prior art with the present dental hygiene device disclosed herein having a distinguishing telescoping fluid chamber in the handle balancing the toothbrush head at the opposite end. Handle fiberoptics optically conveys illumination to the oral area of a user which is also advantageous over the prior art.

A frequently neglected aspect of personal dental hygiene is the adequate irrigation of gums, gingival and sub-gingival tissues. It is important to irrigate the oral cavity for an adequate amount of time with an antiseptic solution. Clinical evidence abounds to show that effective anti-tartar and anti-gingivitis prophylaxis improves with the amount of time the periodontal tissues are exposed to the solution which generally requires at least one or two minutes of irrigation. The amount of irrigation needed depends on whether the objective is prophylaxis or inducing regression of on-going periodontal pathology. Areas of the gum-lines and gums needing more application of brushing and antiseptic irrigation can often be identified by visual inspection. There is thus a need in the field of personal dental hygiene devices for an electric toothbrush assembly that both irrigates and illuminates the periodontal area of interest, such as disclosed in the present invention.

Toothbrush systems with combination brushing and irrigation means are known in the prior art. U.S. Pat. Nos. 5,321,866 and 5,301,381 as well as Patent Application Publication No. 2002-0152565 A1, all by the same inventor as the subject invention; disclose toothbrush systems representing earlier embodiments of brushing and irrigation systems for dental hygiene. Differences between the subject invention system and the inventor's previous Patents and Disclosures include a new concept for the fluid pumping system, removing the handle bellows systems and forming a telescoping fluid chamber on the base end of the toothbrush handle among other concepts as will be further described. The illuminating mechanism as described in the present invention is a further advantage over the prior art.

Other toothbrush systems with a handle reservoir include U.S. Pat. No. 6,669,390; and U.S. Pat. No. 6,575,203, however, such prior art devices include disadvantages as previously referred to above.

U.S. Pat. No. 6,164,967 is directed to a fluid delivering dental cleaning device, which is dissimilar to the subject invention concept with regard to the placement and nature of the fluid reservoir as well as the manner in which the reservoir needs to be filled.

Other Patent references that incorporate telescoping fluid dispensing chambers include U.S. Pat. No. 6,302,305 and U.S. Pat. No. 6,719,729. In these references, the telescoping fluid pump differs structurally as well as in its coupling with a base reservoir coupled to the removable toothbrush assembly as well as the integration with dental specific functionalities.

U.S. Pat No. 6,735,803 is directed to an electrical dentifrice-dispensing toothbrush with a replaceable unit and a refillable cartridge. The device has neither the type of refill system nor the telescoping handle chamber nor the illuminating means as disclosed in the present invention.

The present invention thus fills a need for a personal dental hygiene system in which a user may choose the particular dental hygiene head functions, both by choosing which head to attach to the handle housing and by using the control buttons on the dental hygiene toothbrush assembly to activate and deactivate the brushing and irrigating and illuminating functional options. The invention further discloses an innovative solution to the problem of how to store an irrigating fluid in the device handle and to refill the handle fluid chamber with minimal demands on a user.

SUMMARY OF THE INVENTION

A dental hygiene device is provided where there is included a dental hygiene head having displaceable bristles secured to the dental hygiene head and extending therefrom. This system is adapted for brushing a dental surface within an oral cavity. The dental hygiene head includes an irrigation mechanism for irrigating the dental surface with a fluid which may be antiseptic in composition. The irrigation mechanism is fixedly located adjacent to the displaceable bristles. A longitudinally extended handle housing is connected to the dental hygiene head and is adapted to be held by an operator. The handle housing has a control mechanism mounted on it for activation and deactivation of the dental hygiene device.

Additionally, at least one handle pump is provided for displacing the fluid being passed through the dental hygiene device. The handle pump is mounted in the handle housing and is in fluid communication with the irrigation mechanism through a first fluid conduit.

A telescoping handle member housing is further provided which is slidingly engagable with the handle housing and is telescopingly received therein at a piston end of the handle housing opposite the dental hygiene head and further in fluid communication with the handle pump by a second fluid conduit. The dental hygiene head, handle housing and telescoping handle chamber housing are all in combination defined as a handle assembly.

A fluid reservoir which is in detachable fluid communication with a docking base member is provided. The docking base member is in detachable fluid communication with the telescoping handle chamber housing and the docking base member is adapted to receivingly detachably dock with the handle assembly. In this manner, filling of the telescoping handle chamber with the fluid in the fluid reservoir is achieved and is controlled by at least one base microswitch mechanism formed in the docking base member. The base microswitch mechanism may be magnetically and electrically coupled to at least one handle microswitch mechanism mounted in the handle assembly. The base and handle microswitch mechanisms are in respective functional alignment when the handle assembly is docked on the docking base member.

In further summary of the invention, a dental hygiene device is provided which includes a handle assembly and a docking base member. The handle assembly includes a dental hygiene head, a handle housing and a telescoping handle chamber housing. The docking base member with its fluid reservoir incorporated therein constitutes the docking station for the handle assembly. Placing the handle assembly into the docking base member activates microswitches to refill the telescoping fluid chamber with fluid from the reservoir responsive to the pressure sensed by the microswitches in the docking base member as well as the handle housing. The handle housing is coupled between the dental hygiene head and the telescoping handle chamber housing. The handle housing has control switch mechanisms as well as a motor and connecting elements for causing the bristles located in the dental hygiene head to vibrate, oscillate, and possibly rotate.

The handle housing further includes a pumping mechanism and connections for propelling a fluid such as an antiseptic, antibacterial, fluoride, tartar control, whitening agent or other prescription or over-the-counter fluid based medication.

The handle housing contains a component board mounted thereon with at least one motor, a fluid pump and control switch mechanisms which is further adapted to connect to the dental hygiene head.

The dental hygiene head may be permanently connected to or in the alternative replaceably and interchangeably connectable to the handle housing.

The dental hygiene head includes a multiplicity of bristles fixedly contained thereon and projecting therefrom which are connected to a drive-shaft transferring torque to enable rotary and oscillatory displacement of the bristles.

The driveshaft is then rotatingly connected with a handle brush motor mounted in the handle housing and is mounted preferably on a component board. The dental hygiene head further includes at least one fluid outlet nozzle for directing a flow of the appropriate fluid as previously described to the user's dental, oral and periodontal structures, surfaces and recesses.

The handle housing is fitted between the dental hygiene head and the telescoping handle chamber housing. The handle includes control switch mechanisms as well as a motor and connecting elements for allowing the bristles to be displaced.

Further included is a pumping mechanism and couplings for propelling the fluid. The dental hygiene device in overall concept includes a docking base member with a fluid reservoir and constitutes a docking station for the toothbrush device into the docking base member activating microswitch mechanism to refill the telescoping fluid chamber with fluid from the reservoir responsive to pressure sensed by the microswitch mechanisms in the docking base as well as in the handle housing.

The fluid is pumped through a pump mounted within the handle into a first fluid conduit to reach the fluid outlet nozzle to reach a fluid outlet nozzle. In one embodiment, there is a dedicated handle pump motor mounted on a component board in the handle housing.

In a further embodiment of the invention there is a unitary handle motor and there are provided clutch and gearing mechanisms connected to and interposed between the motor and a driveshaft and further between the motor and the handle pump so as to divide the torqueing force generated by the motor between the driveshaft and the handle pump.

The clutch and gearing mechanisms may use a unitary or single handle motor to power both the handle pump and the driveshaft.

The overall system may include a mechanism for modulating the fluid flow, allowing a user to choose the particular kind of fluid stream projected from the fluid outlet nozzle such as a continuous, pulsatile, rhythmic, fluid discharge pressure and associated fluidic parameters.

A fiber optic illumination subassembly may be provided which provides illumination for a user to visually inspect and observe areas of interest in the oral cavity that may require more intense care. The illumination subassembly is provided at the working end of the dental hygiene head and light is emitted at an illumination head which is optically connected to a light source by an interposed bundle of optically transmissive fibers in the handle housing.

The bundled optically transmissive fibers terminate adjacent the bristles and the fluid outlet nozzle.

The first fluid conduit which may be a flexible non-distensible tubing is formed from or incorporates the bundled optically transmissive filaments. Thus, the first fluid conduit may be a flexible non-distensible optically transmissive cylinder containing a moving fluid which is pumped out of the telescoping handle chamber and delivered under pressure from the fluid outlet nozzle. In such a case, the illumination head projects a cross-sectional ring of light around the fluid stream permitting the user to visually monitor the effectiveness of the dental hygiene procedure.

The handle housing may be formed on a bottom end which is the end opposite the dental hygiene head interface and is formed as a piston to be telescopingly received in the handle fluid chamber. Thus the piston end of the handle housing is displaced with respect to the telescoping handle chamber along a central axis of the handle housing dependent upon the amount of fluid within the chamber.

When the chamber is in a full condition (maximum fluid in the chamber), the telescoping handle chamber is displaced downwardly and away from the dental hygiene head. As the fluid chamber is emptied, the telescoping handle chamber moves toward the dental hygiene head.

The handle housing is further equipped with microswitch mechanisms such as magnetic relay switches to permit electromagnetic communication with a docking base member on which the dental hygiene device is then refilled. The handle housing may be provided with batteries for powering the brush motor and the pump motor. If these batteries are of the rechargeable type, the dental hygiene device may be provided with induction coils in the docking base member and the handle assembly which line up when the docking approximates the respective charging coils in the docking base member with corresponding elements in the handle housing.

Fluid is retained with the docking base member reservoir by a valve until the handle assembly is docked. Once docked, the microswitch mechanisms are triggered to open the unidirectional (or check valve) valve mechanisms as well as to activate the pump in the docking member and thus induce filling of the telescoping handle chamber with fluid from the docking base member reservoir.

Once the telescoping handle chamber has been filled to capacity with fluid, the microswitch mechanisms discontinue the pumping, close the valve or valves and thereby automatically terminate the filling process.

All of the connections for fluid communication from the elements are adapted to be fitted with O-rings to provide substantially leak proof fluid transfers. Additionally, the docking base member fluid reservoir may be equipped with a reservoir illumination device which provides a visual mechanism for a user to assess the relative status of the reservoir aside from any aesthetic appeal.

An important objective of the present invention is to provide a dental hygiene device which requires minimal amount of maintenance by the user.

A further objective of the instant invention is to provide a dental hygiene device which requires minimal behavior modification to accomplish both brushing dental surfaces and applying a pulsating cleansing liquid to areas especially as may be identified by the illuminating element.

Another object of the present invention is to provide in a unitary dental hygiene device a system which replaces a plurality of dental hygiene implements such as a toothbrush and an irrigation device as well as to help a user to visually identify dental areas that may need increased care and attention as disclosed by the illumination provided.

Another object of the subject invention is to provide a dental hygiene system wherein the refilling of the handle chamber with fluid from a reservoir can be accomplished automatically, efficiently, and economically.

DESCRIPTION OF THE PREFERRED EMBODIMENTS

Figure 1:
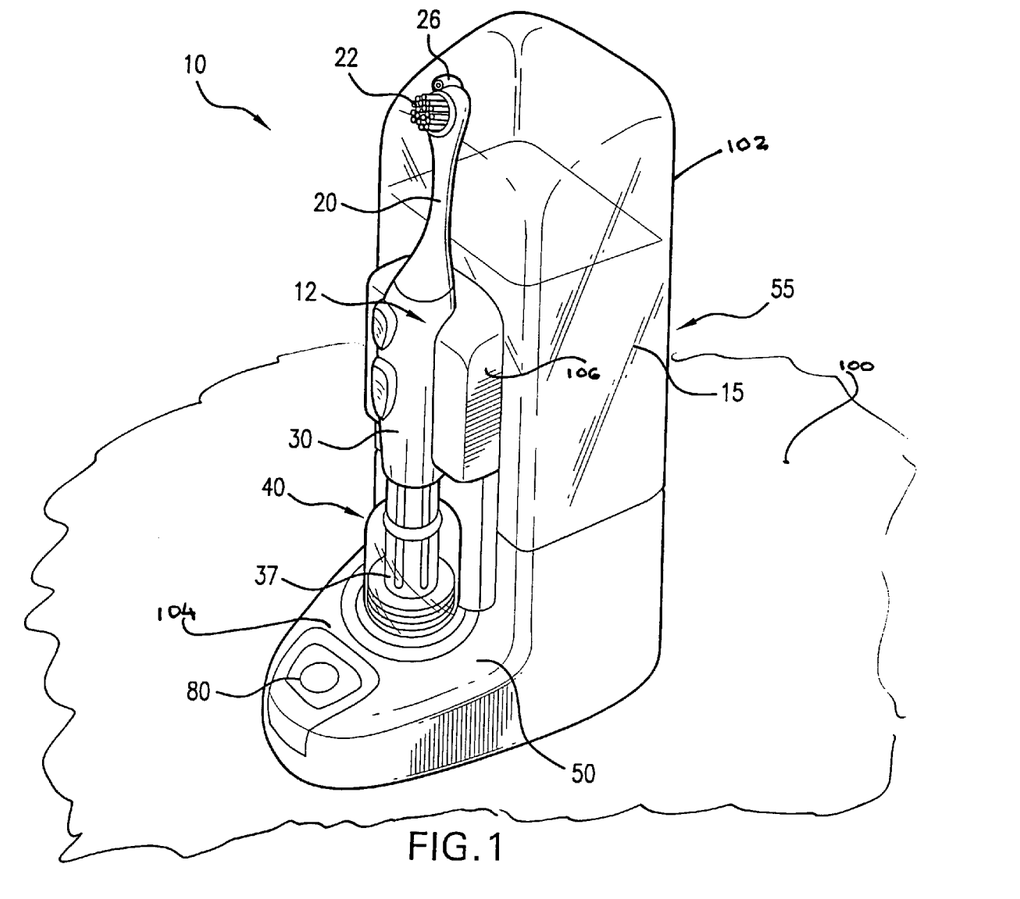
FIG. 1 is a perspective view of the dental hygiene device showing the toothbrush docked in a docking base member.
Figure 6:
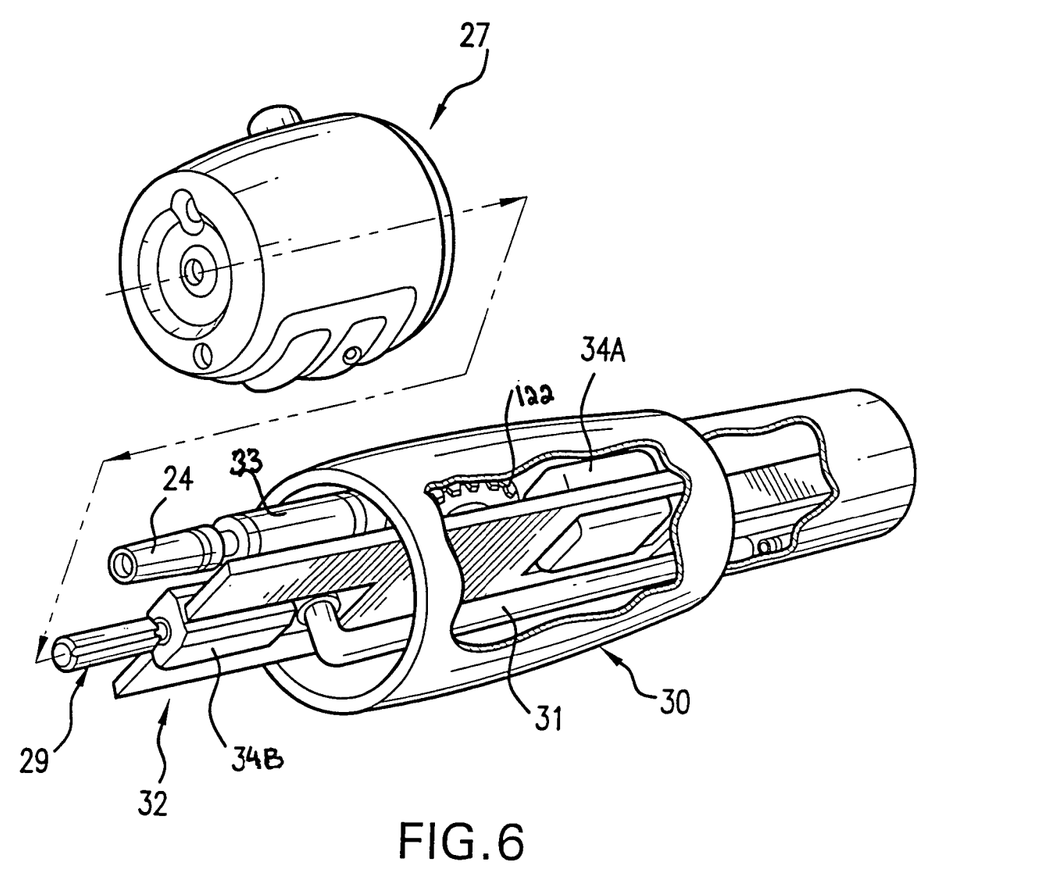
FIG. 6 is an exploded view partially cutaway, of the handle housing with an end cap aligned thereto showing both a pump motor and a brush motor.
Figure 7A:
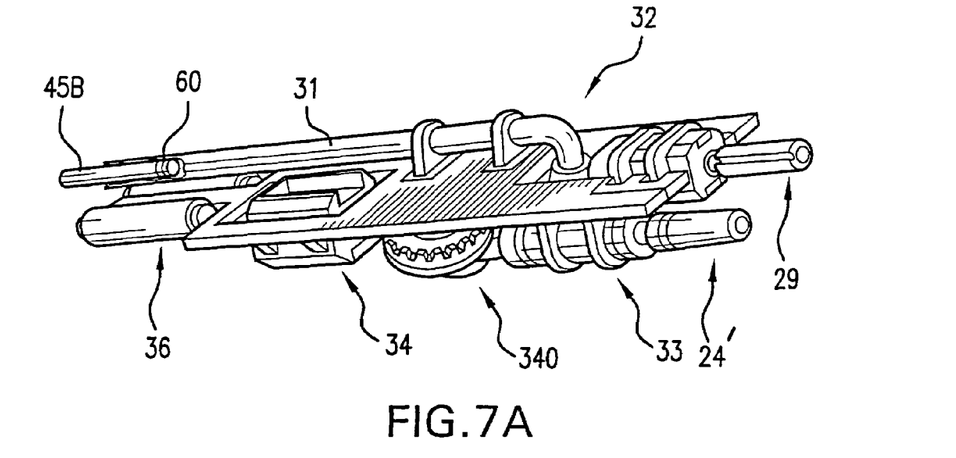
FIG. 7A is a perspective view of the component board which is mounted in the handle housing.
Figure 7B:
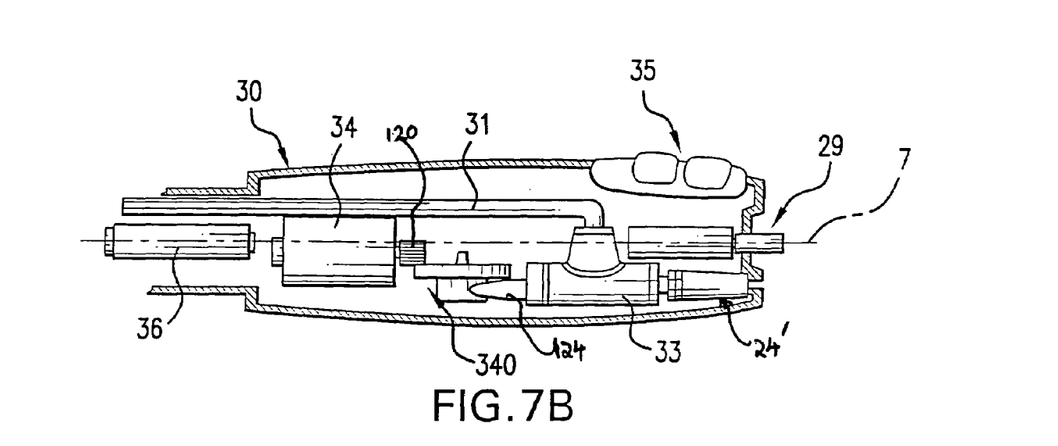
FIG. 7B is a top cross-sectional view of the handle housing.
Figure 7C:
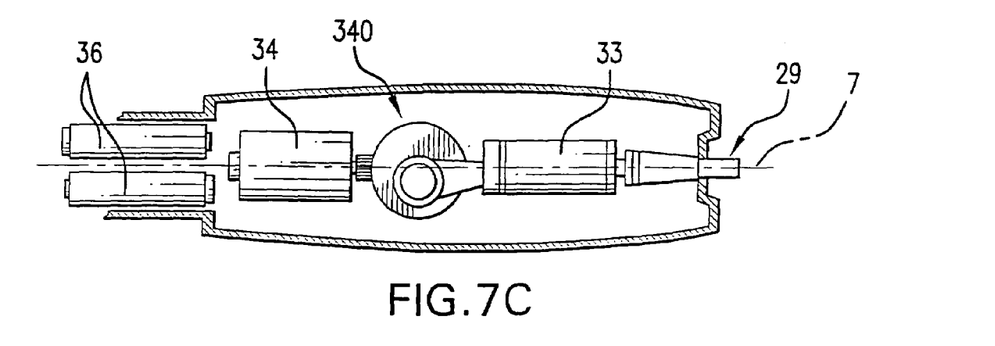
FIG. 7C is side cross-sectional view of the handle housing.
Figure 8:
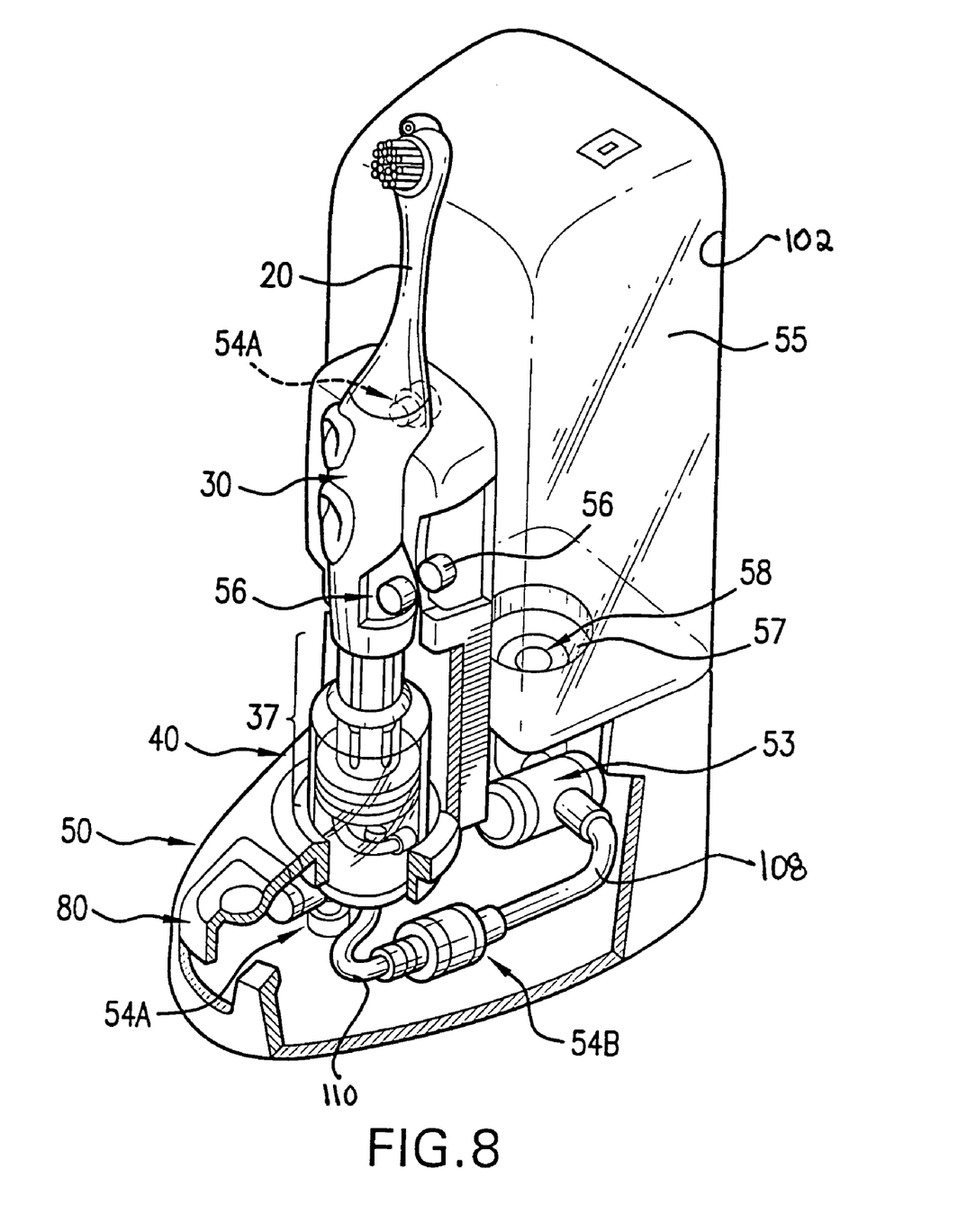
FIG. 8 is a cutaway perspective view of the dental hygiene device.

Referring now to FIGS. 1–8 and particularly with respect to FIGS. 1 and 8, there is shown dental hygiene device 10 which is adapted to be mounted on base surface 100. In dental hygiene device 10 includes docking base member 50 in combination with fluid reservoir housing 55 as shown. The combination of docking base member 50 and fluid reservoir housing 55 is substantially L-shaped in contour for permitting mounting of dental hygiene head 20, handle housing 30 and telescoping handle chamber housing 40 in combination within a base portion of docking base member 50 all combined in a compact and volume efficient manner. As is seen, fluid reservoir housing 55 contains fluid 15 which may be an antiseptic, antibacterial, fluoride, tartar control, whitening agent, or other prescription or over-the-counter fluid based medication, not important to the invention concept with the exception that fluid 15 be adapted to be emitted or passed through dental hygiene device 10 adjacent or through bristles 22 into the oral cavity of a user.

Docking base member 50 and fluid reservoir housing 55 may be formed of a plastic material composition or some like composition not important to the invention concept as herein detailed with the exception that fluid reservoir housing 55 and docking base member 50 be fluid tight to permit maintenance of fluid 15 within fluid reservoir housing 55 without external seepage. Fluid 15 is shown in FIG. 1 to be partially loaded or filled within fluid reservoir chamber 102. It is to be further noted that fluid reservoir housing 55 may be transparent or translucent to permit a user to visually access fluid 15 within fluid reservoir housing 55.

Docking base member 50 includes base actuation mechanism 80 which may be a simple on/off power switch well known in the art. Docking base member 50 includes docking lower base surface 104 within which power mechanism or base actuation mechanism 80 is mounted. Additionally, dental hygiene device 10 includes dental hygiene head 20 coupled to handle housing 30 and telescoping chamber housing 40 which define handle assembly 12 in combination. As is seen in FIGS. 1 and 8, handle assembly 12 is mounted within docking base member 50 and is insertable within U-shaped reservoir housing member 106 secured to an outer wall of fluid reservoir housing 55. In this manner, handle assembly 12 is releasably attached in a confined manner to docking base member 50 and fluid reservoir housing 55 when dental hygiene device 10 is not in use.

As shown in FIGS. 1 and 8, dental hygiene head 20, handle housing 30 and telescoping handle chamber housing 40 are docked or mounted in docking base member 40 which contains fluid reservoir chamber 102. Dental hygiene head 20 as shown includes bristles 22 and further includes fluid outlet nozzle 26 which may be mounted adjacent bristles 22, interspersed within bristles 22, or in some other location not important to the inventive concept as herein described with the exception that fluid 15 be passed from the area adjacent or within dental hygiene head 20 into the oral cavity during use. The structure of dental hygiene head 20, handle assembly 12 and telescoping handle chamber housing 40 may be formed of a lightweight composition such as a plastic composition or some light material not important to the inventive concept as herein described. Fluid outlet nozzle 26 may be formed of plastic or some like material to allow emission of light around a nozzle opening.

Referring now to FIG. 8, fluid 15 within fluid reservoir chamber 102 is passed from fluid reservoir chamber 102 into base pump 53, first base conduit 108, through pressure limit cutoff switch 54B, through second base conduit 110 and eventually into telescoping handle chamber housing 40 to be described in detail in following paragraphs.

Figure 2:
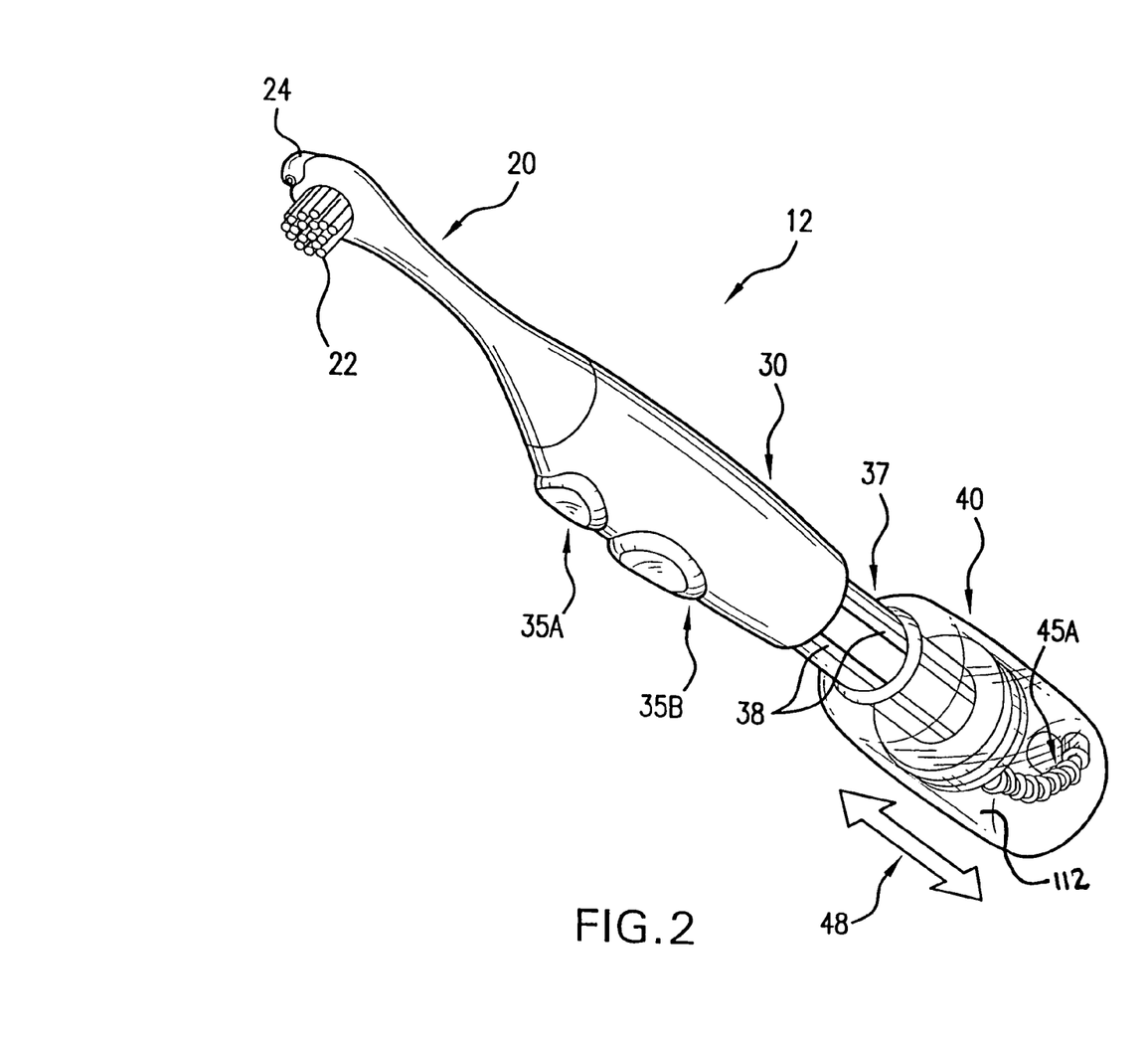
FIG. 2 is a perspective view of the handle assembly showing the dental hygiene head connected to the handle housing and the telescoping handle chamber housing.

Referring now to FIG. 2, handle assembly 12 is shown wherein dental hygiene head 20 is coupled to handle housing 30 which in turn is mounted to telescoping handle chamber housing 40. Fluid 15 which is contained within telescoping handle chamber 112 of telescoping handle chamber housing 40 is passed through siphon hose 45A for fluid communication with a second fluid conduit 31 shown in FIG. 7A. Fluid conduit 31 extends in an axial direction for fluid connection with piston fluid pump 33 shown in FIG. 7B within handle housing 30.

As fluid 15 is charged or displaced from telescoping handle chamber housing 40, handle housing piston end 37 is displaced along guide tracks 38 in a direction indicated by directional arrow 48 shown in FIG. 2. As seen in FIGS. 2 and 3B handle housing 12 includes control switch 35A which is a depressible switch which may be simply a power on/off switch for activating displacement, oscillation and/or rotation of bristles 22. Control switch 35B is a depressible switch member which can interrupt or allow fluid delivery to outlet nozzle 26 for passage of fluid into the oral cavity.

Figure 3A:
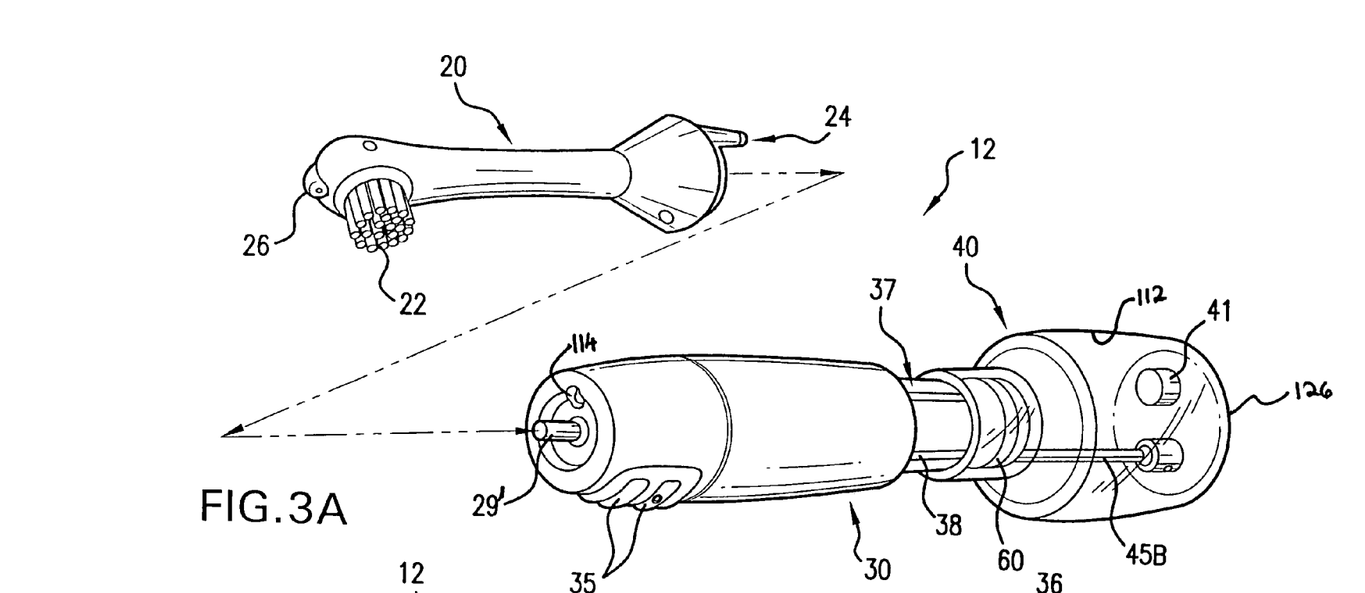
FIG. 3A is a perspective exploded view showing the connection of the dental hygiene head with the handle housing.
Figure 3B:
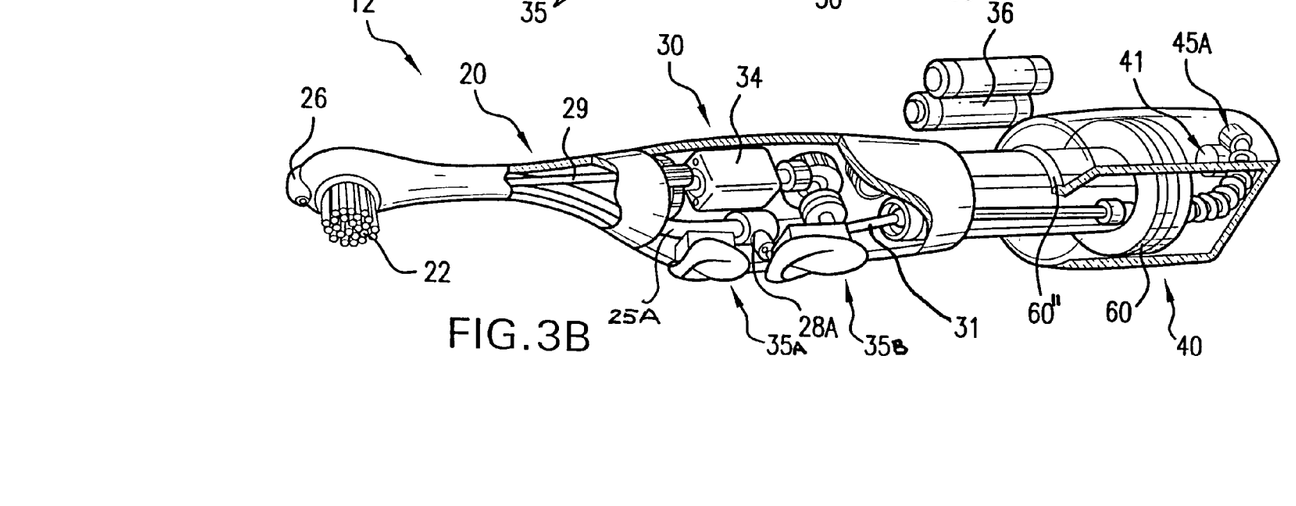
FIG. 3B is a perspective cutaway view of the dental hygiene head connected to the handle housing and telescoping handle chamber housing.

Referring now to FIG. 3A the dental hygiene head 20 is shown in a detached position with respect to handle housing 30. It is understood that in operation, dental hygiene head 20 is mounted to handle housing 30 in a manner wherein dental hygiene head 20 matingly engages first fluid conduit 24 within head opening 114 in a manner to provide fluid communication between dental hygiene head 20 and handle housing 30 for passage of fluid therethrough. As provided in FIG. 7A, first fluid conduit 24 provides for a continuous flow of fluid through first fluid conduit 24 into dental hygiene head 20 for emission from fluid outlet nozzle 26. As seen in FIG. 7A, the fluid path extends from siphon tube 45B through second fluid conduit 31 into first fluid conduit 24' and then further into first fluid conduit 24 formed within dental hygiene head 20.

Second fluid conduit 31 is in fluid communication with siphon tube 45B shown in FIG. 7A and is mounted therein with an O-ring 60 which is used to prevent fluid leakage.

Figure 5:
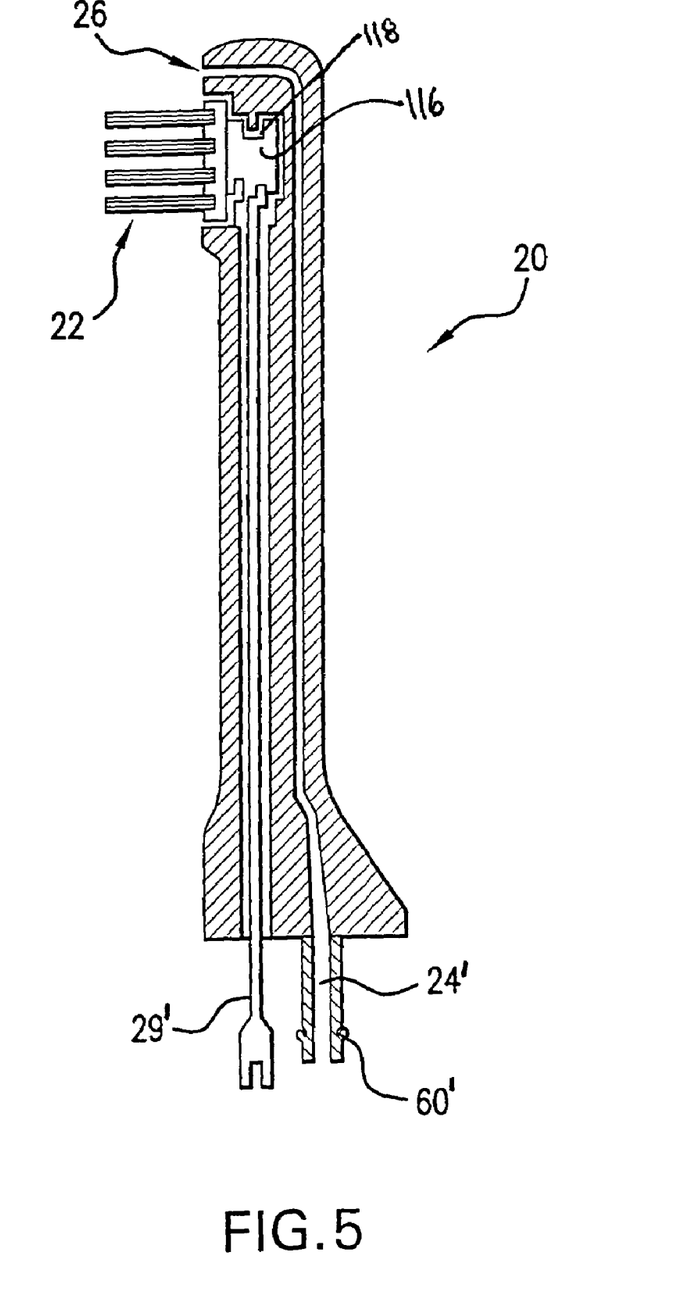
FIG. 5 is an elevation cross-sectional illustration of the dental hygiene head.

Actuation of bristles 22 is more clearly seen in FIG. 5 wherein driveshaft 29 (actuated by motor 34 shown in FIG. 3B) rotates about an axial direction and is coupled to bristle head actuation member 116 which includes cam-like recess 118 which is coupled to driveshaft 29. As driveshaft 29 rotates about the axial direction, bristle head actuation member 116 causes a displacement of bristles 22 in a manner well known in the art. Driveshaft 29 is coupled to motor 34 either directly or through a gear reduction system (not shown). Driveshaft 29 shown in FIG. 5 is adapted to be coupled to driveshaft extension 29' which in itself is coupled to motor 34. First fluid nozzle 24 includes at an end section O-ring 60' shown in FIG. 5 for prevention of leakage of a fluid passing therethrough.

Referring now to FIG. 7A–C, component board 32 is provided in mounted fashion with siphon tube 45B, second fluid conduit 31 and first fluid conduit 24' for passage of fluid therethrough. Each of the aforementioned elements are in fluid communication each with respect to the other. Component board 32 includes motor 34 mounted thereon which, may be actuated by batteries 36 being electrically coupled to motor 34 and actuated in an on/off condition. Motor 34 may be a standard motor which is well known in the commercial field for actuation of dental devices. As is seen in FIG. 7B, motor 34 is coupled to piston 124 through motor gear 120 and motor bevel gear 122 wherein piston member 124 is mounted eccentrically on motor bevel gear 20 for providing linear reversible motion to piston 124 for driving fluid through piston pump 33. In overall context, the combination of motor gear 120, and motor bevel gear 122 may be defined as cam piston coupling 340. In this manner, motor 34 upon actuation drives fluid through piston pump 33 for passage of fluid into first fluid conduit extension 24' of dental hygiene head 20.

Referring now to FIGS. 3A and 3B, telescoping handle chamber housing 30 includes siphon tube 45B extending in an axial direction from a frontal surface of handle chamber housing 40 to a rear surface 126 which includes valve recess 41 formed within recess rear surface 126. Valve recess 41 contains therein a standard ball valve for insert of fluid into chamber 112 which is then passed into siphon tube 45B subsequent to chamber 112 being filled.

In the embodiment shown in FIG. 3A, telescoping chamber housing 40 includes siphon hose 45A which is coupled on opposing ends to siphon tube 45B and inlet from second base conduit 110. In particular, fluid reservoir housing 55 of docking base member 50 is connected to fill the telescoping handle chamber 112. Guide tracks 37 are provided to constrain and facilitate the longitudinal sliding relationship as well as to avoid twisting of various tubes and elements as handle chamber 40 is either emptied or filled.

Figure 4A:
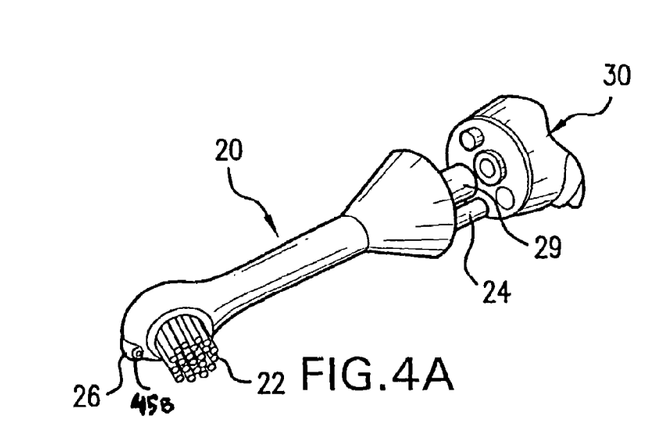
FIG. 4A is a perspective view of the dental hygiene head in relation to the handle housing.
Figure 4B:
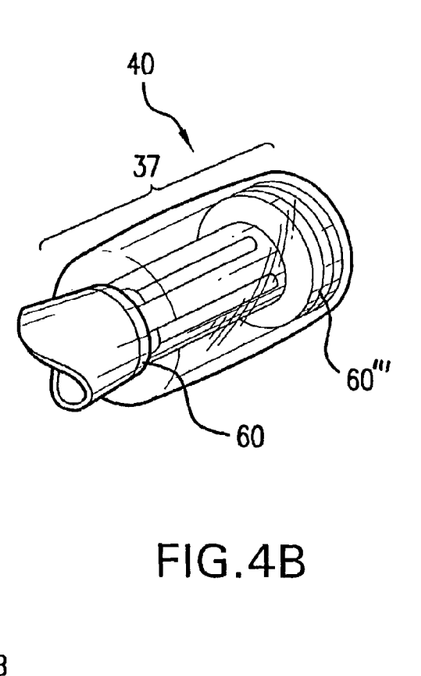
FIG. 4B is a cutaway perspective view of the telescoping handle chamber empty of fluid.
Figure 4C:
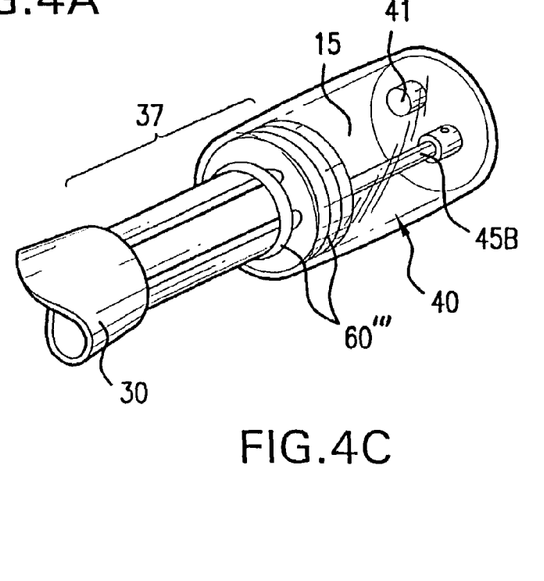
FIG. 4C is a cutaway perspective view of the telescoping handle chamber with the chamber filled with fluid.

As may further be understood, either siphon hose 45A shown in the embodiment provided in FIGS. 2 and 3B or siphon tube 45B of the embodiment shown in FIGS. 3A and 4C transports fluid from the telescoping handle chamber housing to the second fluid conduit 31 and then into pump 33 in handle housing 30.

Referring to FIGS. 4B and 4C such show the full condition and empting condition of telescoping handle chamber 40 with the handle piston end 37 substantially retracted in FIG. 4C where the fluid 15 is substantially filling the telescoping handle chamber housing 40. FIG. 4B is directed to the condition where there is substantially no fluid within telescoping handle chamber housing 40 and the piston end of the handle housing 37 is located at a distal end of the telescoping handle chamber housing. O-rings 60''' provide for fluid tight seal to maintain the fluid in a condition which is substantially leak proof with respect to telescoping handle chamber housing 40. FIG. 6 is directed to an embodiment wherein handle housing 30 is formed with a forward casing end cap 27 which is coupled to the front end of the handle housing 30 for permitting access to component board 32. Component board 32 is mounted internal handle housing 30 with projecting fluid conduit 24 and motor drive 29 that project through apertures in the formed through end cap of 27 for respective alignment of the elements and connection to the driveshaft 29 and first fluid conduit 24 of dental hygiene head 20. As shown in FIG. 6, second fluid conduit 31 transports fluid from telescoping handle chamber of 40 to piston fluid pump 33 mounted on component board 32. Motor 34A is coupled to clutch and gear mechanisms 35 mounted on component board 32. The motor and clutch and gear mechanism 35 are then coupled to an actuate piston pump 33 and motor driveshaft 25.

Referring to FIG. 8 the dental hygiene device 10 with the handle assembly 12 is mounted in the docking base member 50. Microswitches are provided and includes magnetic relay switch 54A and pressure limit cut-off switch 54B formed in-line with the fluid conduit in docking base member 50. Base pump 53 is in fluid communication with fluid reservoir 50 at its outlet where tank release valve mechanism 58 controls flow of fluid 15 out of the reservoir 55. Base pump activation mechanism 80 is a global activation switch for turning on/off dental hygiene device 10.

Figure 9A:
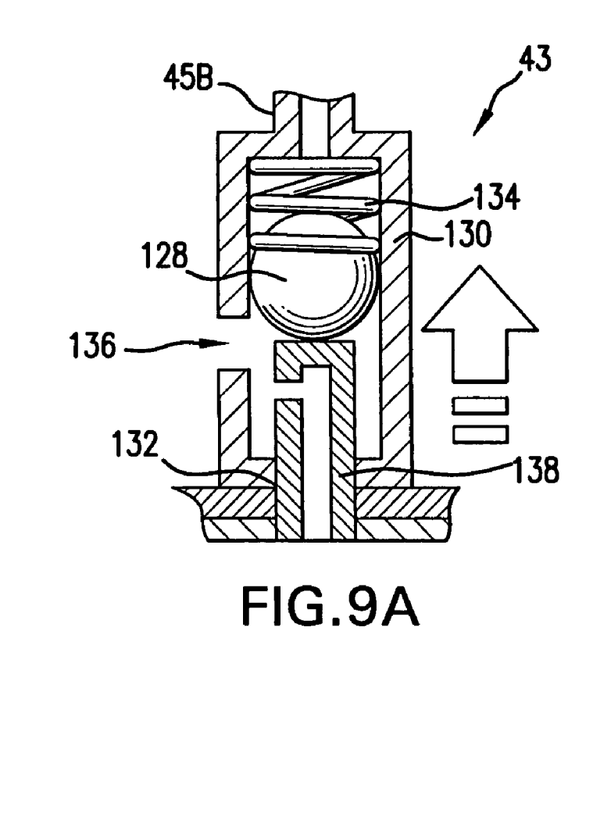
FIGS. 9A and 9B are schematic representations of the ball valve mechanism shown when the handle assembly is mounted on the docking base member 50 and when the handle assembly is removed from the docking base member assembly.
Figure 9B:
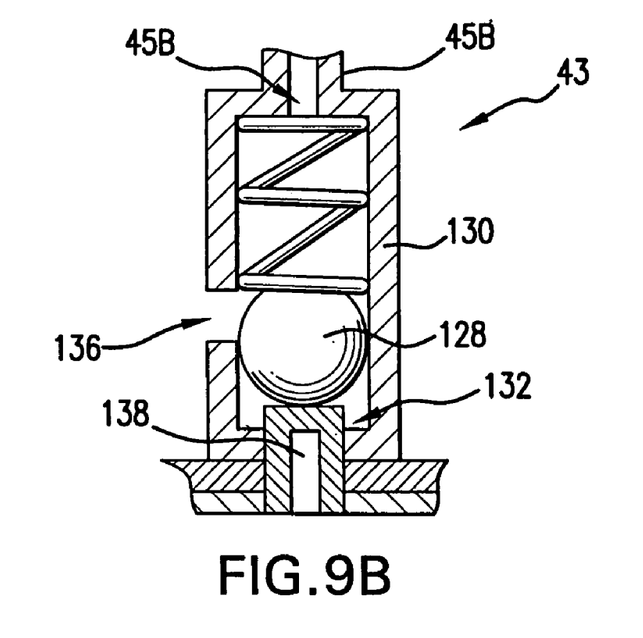

FIG. 9A and FIG. 9B are schematic diagrams of valve control mechanism 43 for controlling flow of fluid 15 from docking base member 50 to telescoping handle chamber housing 40 of a handle assembly 12. Valve mechanism 43 may be a standard check ball valve mechanism which includes ball member 128 mounted within valve housing 130 and having an inlet opening 132 for passage of liquid into chamber 112. Ball 128 is biased by spring member 134 and fluid 15 when assembly 12 is mounted on base 50, shown in FIG. 9A and blocks opening 132. When assembly 12 is removed from base 50, fluid flow into chamber 112 is terminated and fluid within chamber 12 may enter opening 136 for passage threrethrough to siphon tube 45B or into siphon hose 45A as shown respectively in FIGS. 3A and 3B. When assembly 12 is mounted on base 50, ball member 128 is forced upwardly to terminate any flow into assembly 12 but permit flow through conduit 138 and then further through opening 136 into chamber 112. Member 138 may simply be a conduit which extends from base 50 and is in fluid communication with second base conduit 110. Mounting of assembly 12 on base 50 permits locational displacement of ball 128 as has previously been described.

Thus, as is seen in FIGS. 9A and 9B, ball valve mechanism 43 is in physical cooperation with nipple-like projection 138 which extends from docking base member 50 and is received within valve recess 41 of telescoping handle chamber 40 which displaces the spring-biased ball to a closed position. The displacement of ball 128 in an upward direction opens the aperture 136 within the wall of element 130 and provides an open passageway for fluid 15 to be transported from fluid reservoir 55 of the docking base member 50 into the telescoping handle chamber 40. Simultaneously, aperture 134 connecting fluid chamber 40 and siphon tube 45B is closed by the displacement by the ball valve mechanism 43 preventing incoming fluid 15 from entering handle housing 30.

Illumination mechanism for illuminating the oral cavity may be provided for dental hygiene device 10. Light emitting lamp 28A may be mounted internal dental hygiene head 20 and powered by batteries 36. Light from emitting device 28A is transmitted by fiber optic means that comprise a fiber optic bundle 25A formed of an optically transmissive filament combination in alignment. Such may be formed of glass or plastic filaments. Fiber optic bundle 25A and light therein thus extends axially through handle housing 30, through dental hygiene head 20 and terminates adjacent to fluid outlet nozzle 26 and bristles 22. Thus, fluid outlet nozzle 26 may serve both as a light transmissive section surrounding a fluid outlet nozzle opening formed substantially at the center of the fluid outlet nozzle 26.

The illumination of fluid reservoir 55 of docking base member 50 may be provided by a light emitting device 57 in the docking base member 50 either in close proximity to fluid reservoir 55 or in optical communication therewith. Preferred light emitting devices 28A and 57 may include light emitting diodes and/or diodes and/or incandescent and/or halogen light bulbs.

Although this invention has been described in connection with specific forms and embodiments thereof, it would be appreciated if various modifications other than those discussed above may be resorted to without the departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A dental hygiene device comprising:
    a. a dental hygiene head with a plurality of displaceable bristles secured thereto and extending therefrom adapted for brushing a dental surface, said dental hygiene head further including an irrigation mechanism for irrigating said dental surface with a fluid, said irrigating mechanism being fixedly located substantially adjacent to said displaceable bristles;
    b. a longitudinally extended handle housing connected to said dental hygiene head and adapted to be held by an operator, said handle housing having a control mechanism mounted thereon for activation and deactivation of said dental hygiene device;
c. at least one handle pump for displacing said fluid, said at least one handle pump mounted in said handle housing and in fluid communication with said irrigating mechanism through a first fluid conduit;
d. a telescoping handle chamber housing slidingly engageable with said handle housing and telescopingly received therein at a piston end of said handle housing opposite said dental hygiene head and in fluid communication with said handle pump by a second fluid conduit, said dental hygiene head, said handle housing and said telescoping handle chamber housing defining a handle assembly;
e. a fluid reservoir in detachable fluid communication with a docking base member, said docking base member in detachable fluid communication with said telescoping handle chamber housing, said docking base member adapted to receivingly detachably dock said handle assembly;
wherein a filling of said telescoping handle chamber with said fluid in the fluid reservoir is controlled by inserting said telescoping handle chamber housing on said docking base member for passage of fluid from said fluid reservoir into said telescoping handle chamber housing.

2. The dental hygiene device as recited in claim 1 including a bristle actuation mechanism for displacing said bristles in an oscillating displacement.

3. The dental hygiene device as recited in claim 1 including a bristle activation mechanism for displacing said bristles in a rotatable displacement.

4. The dental hygiene device as recited in claim 1, wherein said irrigation mechanism includes at least one fluid outlet nozzle in said dental hygiene head in fluid communication with said first fluid conduit.

5. The dental hygiene device as recited in claim 4, further comprising an illumination mechanism for lighting said dental surface.

6. The dental hygiene device as recited in claim 5 wherein said irrigation mechanism further includes a fluid modulation mechanism for modulating a flow of said fluid external said dental hygiene head.

7. The dental hygiene device as recited in claim 5, wherein said illumination mechanism includes a light emitting device fixedly located interior said handle housing and in optical communication with a fiberoptic bundle extending axially within said handle housing and terminating in said dental hygiene head adjacent said irrigation mechanism.

8. The dental hygiene device as recited in claim 7, wherein said first fluid conduit includes said fiberoptic bundle.

9. The dental hygiene device as recited in claim 1, wherein said dental surface is a surface chosen from the group consisting of gingival, sub-gingival, periodontal, dental, periosteal, buccal, lingual, mucosal, and any combination therein.

10. The dental hygiene device as recited in claim 1, wherein said fluid is chosen from the group consisting of antiseptic, antibiotic, anti-inflammatory, analgesic, anesthetic, antiviral, antifungal, anti-neoplastic fluids or any combination therein, said fluid being in a liquid or a gel or a gaseous condition.

11. The dental hygiene device as recited in claim 1, wherein said handle chamber has a fluid capacity in a range of about 0 to about 100 cc's, corresponding respectively to an empty chamber condition and a full chamber condition.

12. The dental hygiene device as recited in claim 1, further comprising at least one motor mounted in said handle housing for oscillating and rotating said plurality of bristles and for causing said handle pump to displace said fluid.

13. The dental hygiene device as recited in claim 1 including a check valve mechanism mounted in the telescoping handle chamber housing in fluid communication with a chamber formed within the telescoping handle chamber housing and said fluid reservoir.

14. The dental hygiene device as recited in claim 13 wherein said check valve mechanism includes a ball valve mounted within a recess formed in a base surface of said telescoping handle chamber, and a complementary protrusion formed in said docking base member for displacement of said ball valve when said handle assembly is docked on said base unit.

15. The dental hygiene device as recited in claim 14 where said ball valve includes a ball member mounted within a ball housing, said ball member being biased by a spring member for terminating fluid communication between said fluid reservoir and said telescoping handle chamber housing when said telescoping handle chamber housing is removed from said docking base member and providing fluid communication between said fluid reservoir and a chamber formed within said telescoping handle chamber housing when said telescoping handle chamber housing is mounted on said docking base member.

16. The dental hygiene device as recited in claim 1 further comprising a chamber status signal light member mounted in said telescoping handle chamber.

17. The dental hygiene device as recited in claim 16 further comprising a reservoir status signal light member mounted in said fluid reservoir.

18. The dental hygiene device as recited in claim 1 including a base pump in fluid communication with said fluid reservoir and said telescoping handle chamber housing for charging said handle chamber housing with said fluid when said telescoping handle chamber housing is mounted on said docking base member.

19. The dental hygiene device as recited in claim 18 including a pressure limit cut-off switch for terminating operation of said base pump responsive to a predetermined pressure sensed in said telescoping chamber housing.

* * * * *